(12) United States Patent
Kwag et al.

(10) Patent No.: US 7,456,010 B2
(45) Date of Patent: Nov. 25, 2008

(54) MICROORGANISM PRODUCING 5'-XANTHYLIC ACID

(75) Inventors: Young-Hyeon Kwag, Icheon-si (KR); Ki-Hoon Oh, Icheon-si (KR); Jeong-Hwan Kim, Songpa-gu (KR); Yoon-Suk Oh, Yongin-si (KR); Jae-Ick Sim, Icheon-si (KR); Young-Hoon Park, Seongnam-si (KR); Jea-Young Chang, Anyang-si (KR)

(73) Assignee: CJ Cheiljedang Corp., Seoul (KR)

( * ) Notice: Subject to any disclaimer, the term of this patent is extended or adjusted under 35 U.S.C. 154(b) by 300 days.

(21) Appl. No.: 10/531,971

(22) PCT Filed: Dec. 10, 2003

(86) PCT No.: PCT/KR03/02704

§ 371 (c)(1),
(2), (4) Date: Apr. 20, 2005

(87) PCT Pub. No.: WO2004/053110

PCT Pub. Date: Jun. 24, 2004

(65) Prior Publication Data

US 2006/0094084 A1    May 4, 2006

(30) Foreign Application Priority Data

Dec. 11, 2002    (KR)    ...................... 10-2002-0078694

(51) Int. Cl.
*C12N 1/20*    (2006.01)
(52) U.S. Cl. ................................... 435/252.1
(58) Field of Classification Search ........................ None
See application file for complete search history.

(56) References Cited

U.S. PATENT DOCUMENTS 6,821,768 B2 * 11/2004 Kim et al. ................. 435/252.1

FOREIGN PATENT DOCUMENTS

| JP | 42-1477 | 1/1967 |
|----|---------|--------|
| JP | 42-3825 | 2/1967 |
| JP | 42-3838 | 2/1967 |
| JP | 44-20390 | 9/1969 |
| JP | 59-078687 A | 5/1984 |
| JP | 12-295996 A | 10/2000 |
| JP | 01-89980 A | 10/2001 |
| KR | 02-57470 A | 7/2002 |
| KR | 02-57472 A | 7/2002 |

OTHER PUBLICATIONS

Fujio, T., et al; "High level expression of XMP aminase in *E.coli* its application for the industrial production of 5'-guanylic acid"; Biosci Biotechnol Biochem Article; May 1997; 61(5):840-5;' PubMed; National Library of Medicine; Internet—NCBI.

* cited by examiner

*Primary Examiner*—Irene Marx
(74) *Attorney, Agent, or Firm*—Mark E. Stallion; Husch Blackwell Sanders LLP

(57) ABSTRACT

The invention relates to *Corynebacterium ammoniagenes* CJXSP 0201 KCCM 10448 producing 5'-xanthylic acid. More specifically, the invention relates to *Corynebacterium ammoniagenes* CJXSP 0201 KCCM 10448 which is a mutant strain of *Corynebacterium ammoniagenes* KCCM 10340 having a resistance to osmotic pressure. In order to obtain mutant strain having enhanced respiratory activity, the present invention adopted *Corynebacterium ammoniagenes* KCCM 10340 as parent strain and treated it with UV radiation and mutation derivatives such as N-methyl-N'-nitro-n-nitrosoguanidine (NTG) according to ordinary procedure. Therefore, *Corynebacterium ammoniagenes* CJXSP 0201 KCCM 10448 of the present invention makes it possible to overcome growth-standing phase rapidly on early culture and for same period of fermentation, can accumulate 5'-xanthylic acid in culture medium at a high yield and concentration rate.

1 Claim, No Drawings

MICROORGANISM PRODUCING 5'-XANTHYLIC ACID

TECHNICAL FIELD

The invention relates to a microorganism producing 5'-xanthylic acid. More particularly, the invention relates to selecting a mutant strain of *Corynebacterium ammoniagenes* KCCM 10340 in order to enhance growth activity, which can rapidly overcome growth-standing phase on early culture and can accumulate 5'-xanthylic acid in culture medium for same period of fermentation at a high yield and high concentration rate.

BACKGROUND ART

5'-xanthylic acid is an intermediate in the nucleic acid biosynthesis process, which is physiologically important in the body of animals and plants, used in food, medical supplies and other various field. The invention relates to a mutant strain from a known strain *Corynebacterium ammoniagenes* KCCM 10340, producing 5'-xanthylic acid by a direct fermentation method at a high yield and high concentration rate than existing technique.

5'-xanthylic acid is an intermediary product of purine nucleotide biosynthesis process and important material for producing 5'-guanylic acid. A widely used method to produce 5'-guanylic acid having fineness and high quality is microorganism fermentation method which produces 5'-xanthylic acid first and converts it into 5'-guanylic acid enzymatically, therefore, to produce 5'-guanylic acid, corresponding amount of 5'-xanthylic acid is necessary. Conventional methods to produce 5'-xanthylic acid are chemosynthesis, deaminization of 5'-guanylic acid which is produced as a result of decomposition of ribonucleic acid in yeast, a fermentation method to add xanthine as precursor material in fermenting medium, a fermentation method to use a mutant strain of microorganism, a method to add antibiotic material (JP 1477/42 and JP 20390/44), a method to add surfactant (JP 3825/42 and JP 3838/42) and so on. Among these, a direct fermentation method of 5'-xanthylic acid by a mutant strain of microorganism is quite advantageous in terms of industrial aspect. Thus, we inventors developed a mutant strain with increased productivity of 5'-xanthylic acid, by modifying the existing character of *Corynebacterium ammoniagenes* KCCM 10340 into the character of producing 5'-xanthylic acid at a large yield rate.

Most microorganisms reach to the condition that the volume doesn't increase any more when keep on culturing under the constant condition, and especially the concentration of microorganism producing primary metabolite, a growth-dependent product, doesn't increase any more. It is mainly caused by limited supply of dissolved oxygen. Method of enhancing aeration and agitation condition, for removal of the limited supply of dissolved oxygen, is used, but there is technical and economical limit in actual production method. To overcome the limit and increase yield rate and concentration of 5'-xanthylic acid by enhancing the volume of microorganism and various physiological activity, under the limited supply of dissolved oxygen, we inventors thought that the method of producing the novel microorganism showing superior growth under the same condition, would be useful. Thus, the inventors investigated and found out that a mutant strain, which can rapidly overcome growth-standing phase on early and shows superior growth, is most effective, and can produce 5'-xanthylic acid at a high yield and high concentration rate than existing technique, and accomplished in this invention.

DISCLOSURE OF THE INVENTION

The invention relates to *Corynebacterium ammoniagenes* CJXSP 0201 (KCCM-10448) which is a mutant strain of *Corynebacterium ammoniagenes* KCCM 10340, producing 5'-xanthylic acid.

The CJXSP 0201 is obtained by adapting *Coiynebacterium anrnzoniagenes* KCCM 10340 as parent strain by spontaneous mutation method and selecting a mutant strain from them. The spontaneous mutation method is the following. 5 mL of nutrient medium (glucose 20 g/L, peptone 10 g/L, yeast extract 10 g/L, sodium chloride 2.5 g/L, urea 3 g/L, adenine 150 mg/L, guanine 150 mg/L, pH 7.2) was poured into a test tube having diameter of 18 mm and sterilized under pressure according to the common methods. Then, *Cotynebacterium ammoniagenes* KCCM 10340 was seeded into and it was cultured with shaking at 200 rpm, 30° C. for 18 hours and the resultant was used as seed culture. 50 µl of the seed culture was seeded into 500 mL-Erlenmeyer flask for shaking which had been sterilized and 40 mL of minimum medium (glucose 20 g/L, potassium phosphate monobasic 1 g/L, potassium phosphate dibasic 1 g/L, urea 2 g/L, ammonium sulfate 3 g/L, magnesium sulfate 1 g/L, calcium chloride 100 mg/L, ferrous sulfate 20 mg/L, manganese sulfate 10 mg/L, zinc sulfate 10 mg/L, biotin 30 µ/L, thiamine hydrochloride 0.1 mg/L, copper sulfate 0.8 mg/L, adenine 20 mg/L, guanine 20 mg/L, pH 7.2) had been added in. Then, it was cultured with shaking at 200 rpm, 30° C. for 24 hours, and when it reached to early log phase of growth, 50 µl of the culture was seeded into another 500 mL-Erlenmeyer flask for shaking in which 40 mL of the minimum medium had been added. And when it reached to early log phase of growth (Optical Density 0.5 ($\lambda$=562 nm)) again, 50 µl of the culture was seeded into another 500 mL-Erlenmeyer flask for shaking in which the minimum medium had been added again. Such a process, namely subculture was repeated 20 times. The final culture was streaked on petri-dish of the minimum medium containing 1.5% agar and was cultured in 30° C. incubator until colony fonned. Among the colonies, colonies showing rapid growth rate relatively were selected as superior mutant strain. And from them, a strain which shows superior 5'-xanthylic acid productivity and growth rate, was separated, named CIXSP 0201, and it was deposited under Budapest Treaty to the Korean Culture Center of Microorganisms whose address is Hongje-1-dong Seodaemun-gu, Seoul on Nov. 21, 2002 with accession Number KCCM 10448. The time for colony forming is 38 hours in KCCM 10340, a known strain, while CJXSP of the invention 0201 takes 31 hours, therefore CJXSP is a mutant strain having character of superior growth.

BEST MODE FOR CARRYING OUT THE INVENTION

EXAMPLE 1

Used strains: *Corynebacterium ammoniagenes* KCCM 10340, *Corynebacterium ammoniagenes* CJXSP 0201

Seed medium: glucose 30 g/L, peptone 15 g/L, yeast extract 15 g/L, sodium chloride 2.5 g/L, urea 3 g/L, adenine 150 mg/L, guanine 150 mg/L, pH 7.2

Fermentation medium: (1) A medium: glucose 60 g/L, magnesium sulfate 10 g/L, ferrous sulfate 20 mg/L, zinc sulfate 10 mg/L, manganese sulfate 10 mg/L, adenine 30 mg/L, guanine 30 mg/L, biotin 100 µg/L, copper sulfate 1 mg/L, thiamine hydrochloride 5 mg/L, calcium chloride 10 mg/L, pH 7.2 (2) B medium: potassium phosphate monobasic 10 g/L, potassium phosphate dibasic 10 g/L, urea 7 g/L, ammonium sulfate 5 g/L Fermentation method: 5 mL of the seed medium was poured into a test tube having diameter of 18 mm and sterilized under pressure according to the common methods. After the sterilization, a *Corynebacterium ammoniagenes* KCCM 10340 and *Corynebacterium ammoniagenes* CJXOL 0201 were seeded in respectively and it was cultured with shaking at 180 rpm, 30° C. for 18 hours. The resultant was used as seed culture. Then, as fermentation medium, A medium and B medium were sterilized separately under pressure according to the common methods and 29 mL of A medium and 10 mL of B medium were respectively poured into sterilized 500 mL-Erlenmeyer flask for shaking and 1 mL of the above-mentioned seed culture was seeded into and fermented at 200 rpm, 30° C. for 90 hours. After the fermentation was completed, the amount of accumulation of 5'-xanthylic acid in the medium showed that the amount in KCCM 10340 was 23.0 g/L and the amount in CJXSP 0201 was 24.7 g/L. (The concentration of accumulated 5'-xanthylic acid is given by 5'-sodium xanthate.$7H_2O$.)

EXAMPLE 2

Used strains: same as example 1.

Primary seed medium: same as the seed medium of example 1.

Secondary seed medium: glucose 60 g/L, potassium phosphate monobasic 2 g/L, potassium phosphate dibasic 2 g/L, magnesium sulfate 1 g/L, ferrous sulfate 22 mg/L, zinc sulfate 15 mg/L, manganese sulfate 10 mg/L, copper sulfate 1 mg/L, calcium chloride 100 mg/L, biotin 150 μg/L, adenine 150 mg/L, guanine 150 mg/L, thiamine hydrochloride 5 mg/L, antifoaming agent 0.6 mL/L, pH 7.2

Fermentation medium: glucose 151 g/L, phosphoric acid 32 g/L, potassium hydroxide 25 g/L, adenine 198 mg/L, guanine 119 mg/L, ferrous sulfate 60 mg/L, zinc sulfate 42 mg/L, manganese sulfate 15 mg/L, copper sulfate 2.4 mg/L, alaniate 22 mg/L, NCA 7.5 mg/L, biotin 0.4 mg/L, magnesium sulfate 15 g/L, cystinate 30 mg/L, histidinate 30 mg/L, calcium chloride 149 mg/L, thiamine hydrochloride 15 mg/L, antifoaming agent 0.7 mL/L, CSL 27 mL/L, tuna extract 6 g/L, pH 7.3

Primary seed culture: 50 mL of the primary seed medium was poured into 500 mL-Erlenmeyer flask for shaking and sterilized under pressure at 121° C. for 20 minutes. After cooling, *Corynebacterium ammoniagenes* KCCM 10340 and *Corynebacterium ammoniagenes* CJXOL 0201 were seeded into respectively and it was cultured with shaking at 180 rpm, 30° C. for 24 hours.

Secondary seed culture: The secondary seed medium was poured into 5 L-experimental fermentation baths (2 L each) and sterilized under pressure at 121° C. for 10 minutes. After cooling, 50 mL of the above primary seed culture was seeded and cultured with the air supply of 0.5 vvm, at 900 rpm, 31° C., for 24 hours. During the culturing process, the pH level of the medium was kept at 7.3 with adjusting by ammonia solution.

Fermentation method: The fermentation medium was poured into 30 L-experimental fermentation baths (8 L each) and sterilized under pressure at 121° C. for 20 minutes. After cooling, the above secondary seed culture was seeded into (1.5 L each) and cultured with the air supply of 1 vvm, at 400 rpm, 33° C. Whenever the residual sugar level drops below 1% during the culturing process, sterilized glucose was supplied and the total sugar level in the fermentation medium was kept at 30%. During the culturing process, the pH level of the medium was kept at 7.3 with adjusting by ammonia solution and the process took 90 hours. After the fermentation was completed, the amount of accumulation of 5'-xanthylic acid in the medium showed that the amount in KCCM 10340 was 137.2 g/L and the amount in CJXSP 0201 was 146.8 g/L. (The concentration of accumulated 5'-xanthylic acid is given by 5'-sodium xanthate.$7H_2O$.)

INDUSTRIAL APPLICABILITY

The invention adopted *Corynebacterium ammoniagenes* KCCM 10340 as parent strain and treated it UV radiation, mutation derivatives such as N-methy-N'-nitro-n-nitrosoguanidine (NTG) according to ordinary procedure. The KCCM 10340 strain has a resistance to osmotic pressure, caused by high concentration of 5'-xanthylic acid accumulated during culturing process, high concentration of glucose and various carbon source added into culture medium, which results in the high osmotic pressure outside bacterial body, inhibition of normal physiological activity of 5'-xanthylic acid-producing cell and decrease of 5'-xanthylic acid production. In order to obtain a strain having enhanced character of growth activity under the same condition, the invention modified *Corynebacterium ammoniagenes* KCCM 10340 and selected a mutant strain which can rapidly overcome growth-standing phase on early culture, and made it possible to accumulate 5'-xanthylic acid in culture medium at a high yield and high concentration rate for same period of fermentation.

What is claimed is:

1. A biologically pure culture of *Corynebacterium ammoniagenes* CJXSP 0201 (Accession Number: KCCM 10448) which produces 5'-xanthylic acid.

* * * * *